(12) United States Patent
Yu et al.

(10) Patent No.: US 11,401,540 B2
(45) Date of Patent: Aug. 2, 2022

(54) PRODUCTION OF ALGAE-DERIVED POLYUNSATURATED FATTY ACIDS

(71) Applicant: Guangxi Xiaozao Agricultural Technology Co., Ltd., Guangxi (CN)

(72) Inventors: Wei Yu, Guangdong (CN); WeiFang Xi, Guangdong (CN); XiaoLi Wu, Guangdong (CN); HongJia Zhang, Guangdong (CN); Lei Wang, Guangdong (CN)

(73) Assignee: GUANGXI XIAOZAO AGRICULTURE TECHNOLOGY CO., LTD., Guangxi (CN)

(*) Notice: Subject to any disclaimer, the term of this patent is extended or adjusted under 35 U.S.C. 154(b) by 58 days.

(21) Appl. No.: 16/652,482

(22) PCT Filed: Nov. 17, 2017

(86) PCT No.: PCT/CN2017/111631
§ 371 (c)(1),
(2) Date: Mar. 31, 2020

(87) PCT Pub. No.: WO2019/095280
PCT Pub. Date: May 23, 2019

(65) Prior Publication Data
US 2020/0231996 A1  Jul. 23, 2020

(51) Int. Cl.
*C12P 7/64* (2022.01)
*C12N 1/12* (2006.01)
*C12P 7/649* (2022.01)

(52) U.S. Cl.
CPC ............... *C12P 7/649* (2013.01); *C12N 1/12* (2013.01)

(58) Field of Classification Search
None
See application file for complete search history.

(56) References Cited

U.S. PATENT DOCUMENTS

| | | |
|---|---|---|
| 2011/0263886 A1 | 10/2011 | Kale |
| 2013/0129775 A1 | 5/2013 | Shinde et al. |
| 2013/0210093 A1 | 8/2013 | Pottathil |
| 2014/0243540 A1* | 8/2014 | Kadam .................. A61K 36/02 554/207 |

FOREIGN PATENT DOCUMENTS

| | | |
|---|---|---|
| EP | 0292846 A2 | 11/1988 |
| JP | 2016147823 A | 8/2016 |
| JP | 2016160237 A | 9/2016 |
| WO | 2011047095 A1 | 4/2011 |
| WO | 2011159682 A1 | 12/2011 |

OTHER PUBLICATIONS

Bondioli, Paolo; et al; "Oil production by the marine microalgae *Nannochloropsis* sp. F&M-M24 andTetraselmis suecica F&M-M33" Bioresource Technology, 114, 567-572, 2012 (Year: 2012).*
Halim, Ronald; et al; "Extraction of oil from microalgae for biodiesel production: A review" Biotechnology Advances, 30, 709-732, 2012 (Year: 2012).*
Dickinson, Selena; et al; "A review of biodiesel production from microalgae" Clean Technology Environmental Policy, 19, 637-668, 2017 (Year: 2017).*
International Search Report and Written Opinion issued in PCT/CN2017/111631 dated Aug. 23, 2018.
EPO, Supplementary European Search Report for the counterpart EP regional stage application, dated Jun. 10, 2021.

* cited by examiner

*Primary Examiner* — David W Berke-Schlessel
(74) *Attorney, Agent, or Firm* — Duane Morris LLP; Thomas J. Kowalski; Deborah L. Lu (57) ABSTRACT

Disclosed is a method for producing algae-derived polyunsaturated fatty acids, comprising the steps of a) contacting dry algae with ethanol; b) removing ethanol to obtain crude oil; c) subjecting the crude oil to a transesterification reaction with a lower alcohol to generate fatty acid alkyl esters; d) extracting the fatty acid alkyl esters to result in a phase containing fatty acid alkyl esters; e) collecting the phase containing fatty acid alkyl esters; and f) contacting the collected phase with silica gel. Also disclosed is a method for effectively removing impurities, including chlorophyll, fucoxanthin and beta-carotene, from crude algal fatty acid alkyl esters, comprising contacting the crude algal fatty acid alkyl esters with silica gel in hexane.

11 Claims, 2 Drawing Sheets

PRODUCTION OF ALGAE-DERIVED POLYUNSATURATED FATTY ACIDS

TECHNICAL FIELD

The present invention relates to a method for producing algae-derived polyunsaturated fatty acids free or substantially free of impurities, including chlorophyll.

BACKGROUND

Polyunsaturated fatty acids (PUFA), such as omega-3 fatty acids, are vital to everyday life and function. The beneficial effects of omega-3 fatty acids like cis-5,8,11,14,17-eicosapentacnoic acid (EPA) and cis-4,7,10,13,16,19-docosahexaenoic acid (DHA) on lowering serum triglyceride levels are well established. They are also known for other cardioprotective benefits (Dyrberg, et al, ω-3 Fatty Acids: Prevention and Treatment of Vascular Disease; Kristensen, et al., eds., Bi &Gi Publ., Verona-Springer-Verlag, London, pp. 217-26, 1995; O'Keefe and Harris, Am. J. Cardiology 2000, 85:1239-41; Radack et al., The effects of low doses of omega-3 fatty acid supplementation on blood pressure in hypertensive subjects: a randomized controlled trial. Arch. Intern. Med. 1991, 151:1173-1180). The American Heart Association has endorsed the use of omega-3 fatty acids to reduce cardiovascular and heart disease risks. Other benefits of PUFAs include those related to the prevention or treatment of inflammation, neurogenerative diseases, and promoting cognitive development (Sugano, Michihiro, Balanced intake of polyunsaturated fatty acids for health benefits. J. Oleo Sci. 2001, 50(5):305-311).

Recent studies have further shown that EPA, but not DHA, is responsible for some of the reported benefits (Martins J G. EPA but not DHA appears to be responsible for the efficacy of omega-3 long chain polyunsaturated fatty acid supplementation in depression: evidence from a meta-analysis of randomized controlled trials. J Am Coll Nutr. 2009 October; 28(5):525-42.; Eclov J A et al., EPA, not DHA, prevents fibrosis in pressure overload-induced heart failure: potential role of free fatty acid receptor 4. J Lipid Res. 2015 December; 56(12):2297-308. doi: 10.1194/jlr.M062034. Epub 2015 Oct. 4).

The traditional source of omega-3 fatty acids is fish oil. However, with overfishing and concentrated environmental contaminants in fish, as well as aversion of animal food by certain consumers, omega-3 fatty acids from vegetarian sources are becoming increasingly popular. Among the vegetarian sources, algae biomass has shown great promise. Alga's superiority, either as a food supplement feedstock or as raw material for extracting omega-3 fatty acids, arises from a variety of factors, including high per-acre productivity compared to typical terrestrial oil crop plants, making use of otherwise non-productive, non-arable land, amenability to a wide variety of water sources (fresh, brackish, saline, and wastewater), production of EPA and/or DHA, and useful co-products such as polysaccharide, protein, carotenoids and chlorophyll.

Algae, including microalgae, have thick and rigid cell walls typically consisting of polysaccharides and proteins, and cell disruption has been reported to enhance the release of intracellular lipids from microalgae by improving the access of the extracting solvent to fatty acids (Halim, R.; Harun, R.; Danquah, M. K.; Webley, P. A. Microalgal cell disruption for biofuel development. Appl. Energy 2012, 91, 116-121; Cho et al. (2012). Enhancement of lipid extraction from marine microalga, Scenedesmus, associated with high-pressure homogenization process. J Biomed Biotechnol 2012, 359432).

Direct extractions from algal cells without cell disruption using organic solvents have been reported, and lipid extraction efficiency was reported to be dependent on the polarity of the solvent and specific combination of solvent mixture (Lee et al., Comparison of several methods for effective lipid extraction from microalgae. Bioresour. Technol. 2010, 101 (Suppl. 1), S75-S77; Lewis et al., Evaluation of extraction methods for recovery of fatty acids from lipid-producing microheterotrophs. J. Microbiol. Methods 2000, 43, 107-116; Lee et al., Rapid method for the determination of lipid from the green alga Botryococcus braunii. Biotechnol. Tech. 1998, 12, 553-556). An extraction method using ethanol with gentle stirring at room temperature was reported, and the extracted crude lipids are then purified by adding water and hexane to perform a liquid-liquid separation (Yang et al., A novel lipid extraction method from wet microalga Picochlorum sp. at room temperature, marine drugs, 2014, 12, 1258-1270). After the lipid extraction, the debris containing high contents of proteins can be reused for producing bait. Fajardo et al., also used ethanol, followed by hexane, to extract and purify lipids from dried microalgae (Fajardo et al., Lipid extraction from the microalga Phaeodactylumtricornutum. Eur. J. Lipid Sci. Technol. 2007, 2, 120-126.).

U.S. Pat. Pub. No. 20140243540 discloses a method of extracting oil from algae, by drying an algae paste to a predetermined moisture content ranging from between 2.6% and 77.6%; contacting the algae paste with a polar solvent to make an algae-solvent solution and extracting oils from the algae paste into a solvent-oil solution; and separating extracted algal oil from the solvent-oil solution.

One additional problem with the extracted lipid is that the omega-3 fatty acids present naturally in algae are a viscous mixture of triglycerides, glycolipids and phospholipids, which is very hard to concentrate. Thus, the triglyceride, glycolipid and phospholipid forms of omega-3 fatty acids are usually converted to ethyl ester forms in a transesterification reaction first, and then subject to purification processes such as molecular distillation. U.S. Pat. No. 5,130,061 discloses a process for production of EPA and DHA acid esters from crude fish oils, by means of transesterification and a two-step molecular distillation. U.S. Pat. No. 9,187,713 discloses a method for producing fatty acid ethyl esters using a direct transesterification process, wherein dried algal biomass is mixed with hexane and then an ethanol-sulfuric acid solution, and the resultant reaction mixture is refluxed at 60° C. for 6 hours to obtain fatty acid ethyl esters.

Another problem with the prior art algal lipids is the large quantity of chlorophyll contained therein, which makes the algal oil brown or dark green. The concentration of chlorophyll in crude algal oil is about 5,320 to 39,998 ppm, 117 to 3,076 times greater than that in canola oil. The lipo-soluble intracellular chlorophyll is readily co-extracted by hexane into crude oil, and may have serious negative impacts on the downstream processing and oil quality. For example, the presence of chlorophyll complicates silica gel column chromatography, and the presence of chlorophylls also makes the oil more susceptible to photo-oxidation, decreases the storage stability of oil, and causes an off-flavor.

Efforts have been made to remove chlorophyll from algal oils. Conventional methods include physical absorption using silica or clay, organic solvent extraction, supercritical fluid extraction, oxidation treatment and chromatography. However, none of the methods can completely remove all the chlorophyll in an efficient and environmentally friendly way. For example, chromatographic separation is time-consuming. Clays and bleaching earth used in physical absorption typically do not filter well and require the addition of costly filter aids, and uses of clays are associated with significant oil losses. U.S. Pat. No. 5,053,169 describes the use of silica to remove trace contaminants, specifically phospholipids and associated metal ions, as well as chlorophyll A, from Jojoba oil. However, Jojoba oil is originally light gold in color and contains only a slight amount of chlorophyll. It is not known if silica also works for algal oils.

Acid-treated amorphous silica was also reported to be particularly well suited for removing phospholipids and/or chlorophyll from glyceride oils to yield oils having commercially acceptable levels of those contaminants, as described in U.S. Pat. No. 5,059,487. However, the strong acid present in the pores of the silica adsorbent needs to be removed. Due to the difficulties in chlorophyll removal as mentioned above, it is hard to produce algae-derived fatty acids with no or substantially no chlorophyll in an efficient manner.

Thus, there is a need for a new and improved process of isolating and purifying PUFAs from whole algal cells that overcome the various drawbacks as detailed above of the prior art.

SUMMARY OF THE INVENTION

The inventors of the instant invention have surprisingly found that cell disruption before lipid extraction is not only unnecessary but also results in decreased yield and concentration of polyunsaturated fatty acids contained in the extracted crude algal oils, even though oil mass is increased. It has been further discovered that hexane plus silica gel can effectively remove impurities, including chlorophyll, from crude fatty acid ethyl esters. Omega-3 fatty acids free of or substantially free of chlorophyll can be produced from algae in an efficient and convenient way. Further, the silica gel used in impurity removal can be regenerated by simple and straightforward ethanol washes, reducing production costs.

Accordingly, in one aspect, the present invention provides a method for producing algae-derived polyunsaturated fatty acids, comprising the steps of
a) contacting dry algae with ethanol;
b) removing ethanol to obtain crude oil;
c) subjecting the crude oil to a transesterification reaction with a lower alcohol to generate fatty acid alkyl esters;
d) extracting the fatty acid alkyl esters, e.g. using a mixture of hexane and water, to result in a phase containing fatty acid alkyl esters;
e) collecting the phase containing fatty acid alkyl esters; and
f) contacting the collected phase containing fatty acid alkyl esters with silica gel.

Algae are grown in a suitable medium under appropriate light and temperature conditions, and dry algae used in the above process is prepared by flocculating algal cells out of its liquid cultural medium by adjusting the pH of the medium to about pH 10.5 with a flocculation agent, e.g. sodium hydroxide, collecting algal mass via centrifugation or filtration, and then drying the algal mass. The dry algae can be also prepared by flocculating algal cells out of its liquid cultural medium by adjusting the pH of the medium to about pH 10.5 with a flocculation agent, e.g. sodium hydroxide, collecting algal mass via centrifugation or filtration, re-adjusting the pH of the algal mass to about pH 7, and desalting and drying the algal mass.

The dry algae have a water content of 5 wt % or less and have intact cell walls. The algae may be microalgae, e.g., algae belonging to the genus Nannochloropsis. In one embodiment, the algae are Nannochloropsis *salina*.

The contacting in step a) comprises mixing the dry algae in ethanol. The contacting may last for about 30 minutes at about 78° C. The ethanol may be 99.5% ethanol. The ratio of the dry algae to ethanol may be about 1:10 or more and about 1:5 or less by weight. In one embodiment, the ratio is about 1:10 by weight.

Ethanol is removed in step b) by filtration and/or evaporation. In some embodiments, the evaporation is performed in a vacuum rotary evaporator at about 55° C. under a pressure of about −0.07 MPa.

The lower alcohol used in the transesterification may be methanol, ethanol, propanol, butanol, or the combination thereof. In one embodiment, the lower alcohol is ethanol, especially 99.5% ethanol. The transesterification reaction may be performed in the presence of sulfuric acid at about 70° C. for about 2 hours, the ratio of sulfuric acid to the lower alcohol being about 7:100 by volume. The ratio of the lower alcohol to the crude oil is about 5.3:1 by volume.

The fatty acid alkyl esters are extracted in step d) using a mixture of hexane and water. The ratio of the reaction mixture to hexane to water may be about 3:1:1 by volume. The hexane may be n-hexane. Step d) may be performed for one or more times if needed. After extraction, the hexane phase is separated from the water phase by gravity.

The phase containing fatty acid alkyl esters may be collected in step e) by centrifugation or using a separating funnel.

The contacting in step f) comprises mixing the phase containing fatty acid alkyl esters with the silica gel for a period of time sufficient to remove impurities. The ratio of the phase containing fatty acid alkyl esters to silica gel may be about 5:1.5 (ml/g, v/w) or more and about 5:0.75 or less. In some embodiments, the ratio of the phase containing fatty acid alkyl esters to the silica gel is about 5:0.75, 5:1, or 5:1.5. In preferable embodiments, the ratio of the phase containing fatty acid alkyl esters to the silica gel is about 5:1 or 5:0.75. The silica gel used in step f) is of about 60 to 100 mesh.

The method of the present invention may further comprise, subsequent to silica gel contact, recovering the silica gel from the phase containing fatty acid alkyl esters by filtration, and the recovered silica gel can be regenerated with ethanol washes.

The method of the present invention may further comprise, subsequent to silica gel contact, subjecting the phase containing fatty acid alkyl esters to further refining. The further refining comprises molecular distillation and/or chromatographic separation.

The fatty acid alkyl esters may comprise EPA alkyl ester, DHA alkyl ester, and ARA (arachidonic acid) alkyl ester. In some embodiments, the fatty acid alkyl esters comprise EPA ethyl ester, DHA ethyl ester, and ARA ethyl ester.

In a second aspect, the present invention provides a method for effectively removing impurities, including chlorophyll, fucoxanthin and beta-carotene, from crude algal fatty acid alkyl esters, comprising contacting the crude algal fatty acid alkyl esters with silica gel in hexane.

The contacting comprises mixing the crude algal fatty acid alkyl esters with silica gel in hexane for a period of time sufficient to remove impurities. The ratio of the crude fatty acid alkyl esters to hexane may be about 1:4 by volume. The ratio of the crude fatty acid alkyl esters to the silica gel is about 1:1.5 (ml/g, v/w) or more and about 1:0.75 or less. In some embodiments, the ratio of the crude fatty acid alkyl esters to the silica gel is about 1:0.75, 1:1, or 1:1.5. In preferable embodiments, the ratio of the crude fatty acid alkyl esters to the silica gel is about 1:1 or 1:0.75. The silica gel may be of about 60 to 100 mesh. After the contacting, the silica gel may be recovered by filtration and regenerated with ethanol washes. In some embodiments, the hexane is n-hexane.

The crude algal fatty acid alkyl esters may be obtained from a transesterification reaction of crude algal oil with a lower alcohol selected from the group consisting of methanol, ethanol, propanol, and butanol. In one embodiment, the lower alcohol is ethanol, especially 99.5% ethanol. The transesterification reaction may be performed at the presence of sulfuric acid at about 70° C. for about 2 hours, wherein the ratio of the lower alcohol to the crude algal oil is about 5.3:1 by volume, and the ratio of sulfuric acid to the lower alcohol is about 7:100 by volume.

The fatty acid alkyl esters generated in the transesterification reaction may extracted by using a mixture of hexane and water prior to impurity removal. The ratio of the reaction mixture to hexane to water is about 3:1:1 by volume. The hexane phase containing fatty acid alkyl esters may be separated from the water phase by gravity and collected by centrifugation or using a separating funnel.

The fatty acid alkyl esters may comprise EPA alkyl ester, DHA alkyl ester, and ARA alkyl ester. In some embodiments, the fatty acid alkyl esters may comprise EPA ethyl ester, DHA ethyl ester, and ARA ethyl ester.

In a third aspect, the present invention provides a composition for effectively removing impurities, including chlorophyll, fucoxanthin and beta-carotene, from crude algal fatty acid alkyl esters, comprising silica gel and hexane.

The silica gel is of about 60 to 100 mesh, and can be regenerated with ethanol washes after impurity removal.

The hexane may be n-hexane.

When used, the composition contacts with crude algal fatty acid alkyl esters for a period of time sufficient to remove impurities.

The ratio of silica gel to hexane is about 0.75:4 (g/ml, w/v) or more and about 1.5:4 or less. In some embodiments, the ratio of silica gel to hexane is about 1.5:4, 1:4 or 0.75:4. In preferable embodiments, the ratio of silica gel to hexane is about 1:4 or 0.75:4.

The crude algal fatty acid alkyl esters may be obtained from a transesterification reaction of crude algal oil with a lower alcohol selected from the group consisting of methanol, ethanol, propanol, and butanol. In one embodiment, the lower alcohol is ethanol, especially 99.5% ethanol. The transesterification reaction may be performed at the presence of sulfuric acid at about 70° C. for about 2 hours, wherein the ratio of the lower alcohol to the crude algal oil is about 5.3:1 by volume, and the ratio of sulfuric acid to the lower alcohol is about 7:100 by volume.

The fatty acid alkyl esters generated in the transesterification reaction may be extracted by using a mixture of hexane and water prior to impurity removal. The ratio of the reaction mixture to hexane to water is about 3:1:1 by volume. The hexane phase containing fatty acid alkyl esters may be separated from the water phase by gravity and collected by centrifugation or using a separating funnel.

The fatty acid alkyl esters may comprise EPA alkyl ester, DHA alkyl ester, and ARA alkyl ester. In some embodiments, the fatty acid alkyl esters may comprise EPA ethyl ester, DHA ethyl ester, and ARA ethyl ester.

In the present invention, silica gel is used to remove impurities such as chlorophyll from crude algal fatty acid alkyl esters at the presence of hexane. It has been found that the impurity removal step can be performed within a short time, resulting in fatty acid alkyl esters free of or substantially free of chlorophyll. Other impurities are also removed together with chlorophyll, with carotenoids remained, which will be removed later. When a preferred ratio of the silica gel to the crude algal fatty acid alkyl esters is adopted, a relatively high yield and/or concentration of PUFA alkyl esters such as EPA alkyl esters remain in the purified fatty acid alkyl esters. With advantages above, the present invention may be applicable on large or even industrial scale.

DETAILED DESCRIPTION OF THE INVENTION

Before particular embodiments of the present invention are disclosed and described, it is to be understood that this invention is not limited to the particular process and materials disclosed herein as such may vary to some extent. It is also to be understood that the terminology used herein is used for the purpose of describing particular embodiments only and is not intended to be limiting, as the scope of the present invention will be defined only by the appended claims and equivalents thereof.

In describing and claiming the present invention, the following terminology will be used.

The singular forms "a," "an," and "the" include plural referents unless the context clearly dictates otherwise. Thus, for example, reference to "a step" includes reference to one or more of such steps.

As used herein, the term "PUFA" or "polyunsaturated fatty acid" refers to any fatty acid containing more than one double bond in the backbone, including omega-3 fatty acids. PUFAs may be in cis- and/or trans-configuration.

As used herein, the term "omega-3 fatty acid" refers to a class of PUFAs with a double bond at the third carbon atom from the end of the carbon chain. The three types of omega-3 fatty acids involved in human physiology are arachidonic acid (ARA), eicosapentaenoic acid (EPA), and docosahexaenoic acid (DHA). Algae-derived omega-3 fatty acids have natural triglyceride, glycolipid, and phospholipid forms. The three natural forms, together with some free fatty acids, can be converted to ethyl esters in a transesterification reaction, the ethyl esters being available in U.S. as prescription product and dietary supplement.

As used herein, the term "flocculation" refers to a process where algae come out of suspension in the form of flocs while the term "de-flocculation" refers to a process that is the exact opposite of flocculation where the flocculated flocs become dispersed.

As used herein, the term "dry algae" refers to algae having a water content of 5 wt % or less.

As used herein, the terms "transesterify", "transesterifying" and "transesterification" refer to a process of exchanging an alkoxy group of an ester by another alcohol and more specifically, of converting algal oil, e.g. triglycerides, to fatty acid alkyl esters and glycerol. The transesterification can be performed by using traditional chemical processes such as acid or base catalyzed reactions, or by using enzyme-catalyzed reactions.

As used herein, the term "silica gel" refers to a granular, vitreous, porous form of silicon dioxide. It is non-toxic, non-flammable, and non-reactive and stable with ordinary usage.

As used herein, the term "chlorophyll" refers to any of several closely related green pigments found in cyanobacteria and the chloroplasts of algae and plants. Chlorophyll is essential in photosynthesis, allowing plants to absorb energy from light.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a weight range of about 1% to about 20% should be interpreted to include not only the explicitly recited concentration limits of 1% to about 20%, but also to include individual concentrations such as 2%, 3%, 4%, and sub-ranges such as 5% to 15%, 10% to 20%, etc.

PUFA and Omega-3 Fatty Acid

PUFAs are the subject of intensive researches due to the important health benefits associated with their consumption. These include the α-Linolenic acid (ALA 18:3 ω-3), γ-Linolenic acid (GLA, 18:3 ω-6), eicosapentaenoic acid (EPA, 20:5 ω-3), arachidonic acid (ARA, 20:6 ω-6) docosapentaenoic acid (22:5 ω-3) and docosahexaenoic acid (DHA, 22:6 ω-3). According to Adarme-Vega and colleagues, these long chain omega-3 PUFAs provide significant health benefits particularly in reducing cardiac diseases such as arrhythmia, stroke and high blood pressure (Adarme-Vega T C, Lim D K Y, Timmins M, Vernen F, Li Y. Schenk P M. Microalgalbiofactories: a promising approach towards sustainable omega-3 fatty acid production. Microb Cell Factories. 2012; 11:1-10). As well, they have beneficial effects against depression, rheumatoid arthritis, asthma and can be used for treatment of inflammatory diseases such as rheumatoid arthritis, Crohn's disease, ulcerative colitis, psoriasis, lupus and cystic fibrosis. Additionally, in pregnant women, the adequate intake of EPA and DHA is crucial for healthy development of the fetal brain. In addition, ARA and DHA are required for normal growth and brain functional development, while EPA is essential for the regulation of some biological functions and prevention of arrhythmia, atherosclerosis, cardiovascular disease and cancer (Pulz M O. Gross W. Valuable products from biotechnology of microalgae. ApplMicrob Biotech. 2004; 65:635-648).

Fish oil is a major non-sustainable source for the commercial production of omega-3 fatty acids. Fish oil quality depends on the fish species, the season/climate and geographical location of catching sites and food quality consumed by the fish. In addition, fish oil is not suitable for vegetarians, and its odor makes it unattractive for consumption. In some cases, there is a contamination danger by lipid-soluble environmental pollutants (Ryckebosch E, Bruneel C, Muylaert K. Foubert I. Microalgae as an alternative source of omega-3 long chain polyunsaturated fatty acids. Lipid Technol. 2012; 24:128-130). Thus, algae turn out to be the alternative source for PUFAs like omega-3 fatty acids.

Algae can store energy in its cell structure in the form of either oil or starch. Stored oil can be as much as 60% of the weight of the algae. Certain species which are highly prolific in oil or starch production have been identified, and growing conditions have been tested. In algae, EPA is found in the Bacillariophceae (diatoms) Chlorophyceae, Chrysophyseae, Cryptophyceae, Eustigamatophyceae and Prasinophyceae classes (Singh S, Kate B N. Banerjee U C. Bioactive compounds from cyanobacteria and microalgae: an overview. Crit Rev Biotechnol. 2005; 25:73-95).

In the present invention, Nannochloropsis *salina* is cultured in South China and used to produce fatty acids especially PUFAs. This species is rich in EPA and also contains a small proportion of other fatty acids such as $C_{16:1}$ and $C_{16:0}$ fatty acids. DHA level in this species is negligible. Other Nannochloropsis species also produce a large amount of EPA with almost no DHA.

Flocculation and De-flocculation

Before lipid extraction, algal biomass is flocculated, de-flocculated, desalted and dried.

In particular, the algae are first flocculated out of its liquid cultural medium by adjusting the pH of the medium to about pH 10.5 with a flocculation agent, e.g. sodium hydroxide. Algal mass is collected via centrifugation or filtration, and then de-flocculated by adjusting its pH to about pH 7, desalted, and then dried.

The flocculation process is mainly used to reduce the volume of algae-containing cultural medium to be treated in a separator or a filter, which accelerates the algae collection procedure and prolongs the service life of the separator or the filter. After the pH value of the cultural medium becomes 10 or 10.5, algae begin to settle down. The sediment can be collected later using a separator. It is noted that when the artificial sea water is used instead of real sea water as the cultural medium, less flocculation agent is needed because the artificial sea water contains fewer ions that will react with $OH^-$. For example, about 550 g of NaOH is needed for 1 ton of algae-containing real sea water, while only about 200 to 300 g is needed for 1 ton of algae-containing artificial sea water. In some embodiments, part of the flocculation agent can be added first until the cultural medium has a pH value of, e.g., 10, and the liquid medium is moved to another container by a pump or the like, leaving the formed solids in place. The algal biomass continues to flocculation in the new container with addition of further flocculation agent.

The de-flocculation process aims to reduce or remove salts, metal hydroxides and metal oxides contained in the algal biomass, which impurities may make the final product not qualified as a dietary supplement or a pharmaceutical ingredient. When diluted HCl is added, the solids formed by the ions contained in the original cultural medium and the flocculation agent is dissolved in the solution, which was discarded with the upper water layer after the centrifugation.

Lipid Extraction

Currently, algal oil extraction procedures include mechanical pressing, homogenization, milling and solvent extraction. The most common solvents for lipid extraction are chloroform-methanol, hexane, hexane-isopropanol or other solvent mixtures slightly soluble in each other. Depending on polarity and/or solubility of the lipid content, the proper solvent or mixture must be chosen for the extraction.

The instant invention adopts an environmentally friendly extraction method by using ethanol, the ethanol being 99.5% ethanol or more purified ethanol. Ethanol is considered as a cheap and safe solvent, and has a strong affinity to the lipid complex.

In particular, dry algae contact with 99.5% ethanol with stirring. The ratio of the dry algae to ethanol, and the time and temperature for contact can be determined and adjusted by those skilled in the art, depending on algal species and some other factors. The ratio of the dry algae to 99.5% ethanol by weight may be 1:20 or more, 1:18 or more, 1:16 or more, 1:14 or more, or 1:12 or more, and 1:8 or less, 1:7 or less, 1:6 or less, 1:5 or less, or 1:4 or less. In one embodiment, the ratio is 1:10 or more and 1:5 or less. In one embodiment, the ratio is 1:10. When the ratio is set as 1:10, EPA recovery in the extraction step is about 80%. When the ratio is adjusted to 1:5, EPA recovery is reduced to about 62%.

The contact between the dry algae and ethanol may last for 10 min or more, 20 min or more, 30 min or more, 1 hour or more, or 2 hours or more, and 5 hours or less, or 4 hours or less. In one embodiment, the dry algae contact with 99.5% ethanol for 30 min. The contact may be performed at a temperature ranging from 60 to 85° C., preferably 78° C.

Prior to contact with ethanol, the algae are dried. Wet algae may bring water, which reduces the extraction efficiency and/or complicates the ethanol recycle process.

After lipid extraction, ethanol may be removed by filtration and/or evaporation.

Cell disruption has been reported to enhance the release of intracellular lipids from microalgae by improving the access of the extracting solvent to fatty acids. Thus, in order to gather more fatty acids or PUFAs, the inventors ground the algae to about 2 to 3 μm in size to break the cell walls. Surprisingly, it is found that, despite of a higher crude oil yield, less fatty acids especially less EPAs were obtained as a result, compared to unground algae. Thus, in the instant invention, to produce an EPA-containing product with a high EPA yield and recovery, algae are preferred to be crude algae with intact cell walls.

Lipid Quantification

The methods for lipid quantification are well known in the art. Most literatures reporting lipid determination commonly use chromatography with flame-ionization detectors. Some other techniques are currently used such as fluorometry, colourimetry, Raman spectroscopy, gas chromatography with mass spectrometric detector, high performance liquid chromatography (HPLC) with pulsed amperometric detection, reverse phase HPLC, UV detection at 205 nm, evaporative light scattering detection, atmospheric pressure chemical ionization mass spectrometry, nuclear magnetic resonance, near infrared and Fourier transform infrared spectroscopy (Cooksey, K. E., Guckert, J. B., Williams, S. A., and Callis, P. R. (1987) Fluorometric determination of the neutral lipid content of microalgal cells using Nile Red. J Microbiol Methods 6: 333-345; Lee, S. J., Yoon, B.-D., and Oh, H.-M. (1998) Rapid method for the determination of lipid from the green alga Botryococcusbraunii. Biotechnol Tech 12: 553-556; Knothe, G. (2001) Analytical methods used in the production and fuel quality assessment of biodiesel. Trans ASAE 44:193-200; Meher, L. C., VidyaSagar, D., and Naik, S. N. (2006) Technical aspects of biodiesel production by transesterification—a review. Renew Sustain Energy Rev 10: 248-268; Elsey, D., Jameson, D., Raleigh, B., and Cooney, M. J. (2007) Fluorescent measurement of microalgal neutral lipids. J Microbiol Methods 68: 639-642; Huang, Y. Y., Beal, C. M., Cai, W. W., Ruoff, R. S., and Terentjev, E. M. (2010) Micro-Raman spectroscopy of algae: composition analysis and fluorescence background Behavior. BiotechnolBioeng 105: 889-898; Laurens, L. M. L., and Wolfrum, E. J. (2010) Feasibility of spectroscopic characterization of algal lipids: chemometric correlation of NIR and FTIR spectra with exogenous lipids in algal biomass. Bio Energy Res 4: 22-35; Wawrik, B., and Harriman, B. H. (2010) Rapid, colorimetric quantification of lipid from algal cultures. J Microbiol Methods 80: 262-266; Cheng, Y.-S., Zheng, Y., and VanderGheynst, J. (2011) Rapid quantitative analysis of lipids using a colorimetric method in a microplate format. Lipids 46: 95-103; Davey, P. T., Hiscox, W. C., Lucker, B. F., O'Fallon, J. V., Chen, S., and Helms, G. L. (2012) Rapid triacylglyceride detection and quantification in live microalgal cultures via liquid state 1H NMR. Algal Res 1: 166-175; De la HozSiegler, H., Ayidzoe, W., Ben-Zvi, A., Burrell, R. E., and McCaffrey, W. C. (2012) Improving the reliability of fluorescence-based neutral lipid content measurements in microalgal cultures. Algal Res 1: 176-184).

In the present application, GC analysis is used for lipid quantification.

Transesterification

The crude algal oil is not ideal for use as a food supplement directly because the desired PUFAs like EPA and DHA are in low concentrations.

The PUFAs in the algal oil are a mixture of natural triglycerides, glycolipids and phospholipids. For example, the omega-3 fatty acids in Nannochloropsis *salina* comprises about 23% of triglycerides, about 59% of glycolipids and about 18% of phospholipids, with little free fatty acids. All of the three natural omega-3 fatty acids have large molecular weights. The processes such as lipid separation and purification of the viscous crude oil are time-consuming, and the large molecule weights of the PUFAs makes conditions for molecule distillation extremely harsh. Thus, in order to concentrate EPA and/or other PUFAs, for instance, a transesterification reaction may be done to convert the three natural forms together with free fatty acids to the alkyl ester form.

In prior art, transesterification of triglycerides to produce esters has been performed using catalyst/conditions, such as enzymes (Fjerbaek et al., A Review of the Current State of Biodiesel Production Using Enzymatic Transesterification, Biotechnology and Bioengineering, April 2009, vol. 102, No. 5, pp. 1298-1315; Modi et al., Lipase-mediated Conversion of Vegetable Oils into Biodiesel Using Ethyl Acetate as Acyl Acceptor, Bioresource Technology, 98,2007, pp. 1260-1264); acid/base catalysts (Rodri et al, Biodiesel Fuels from Vegetable Oils: Transesterification of CynaraCarduculus L. Oils with Ethanol (7), 443-450; Alamu et al., "Effect of Ethanol-palm Kernel Oil Ratio on Alkali-catalyzed Biodiesel Yield," Fuel, 87, 2008, pp. 1529-1533); or heterogeneous catalysts (Zabeti et al., Activity of Solid Catalysts for Biodiesel Production: A Review, Fuel Processing Technology, 90, 2009, pp. 770-777).

In the instant application, the transesterification reaction is done with a low alcohol selected from the group consisting of methanol, ethanol, propanol and butanol. In one embodiment, the lower alcohol is ethanol, especially 99.5% ethanol. The purity of ethanol is preferred to be higher than or equal to 99.5%. The reaction conditions can be determined and/or adjusted by those skilled in the art. For example, sulfuric acid can be used to catalyze the reaction, with the ratio of sulfuric acid to the lower alcohol being 7:100 by volume. In some embodiments, the transesterification reaction is performed at 70° C. for 2 hours. In some embodiments, the ratio of the lower alcohol to the crude oil is 5.3:1 by volume.

If the algae, but not the lipid extracted from the algae, undergo a transesterification reaction directly, despite of shorted time, PUFA yield and concentration would be significantly decreased in the crude fatty acid alkyl esters. Further, the algal proteins and polysaccharides are polluted by the reactants and/or sulfuric acid, and more complicated processes are required for purification of these by-products.

Therefore, in the present invention, the transesterification reaction is preferably performed on algal oil extracted from algal powder using ethanol.

Extraction of Fatty Acid Alkyl Ester

After transesterification, the fatty acid alkyl ester is separated from the catalyst and some other water-soluble impurities by using hexane and water. The ratio of the reaction mixture to hexane to water can be determined by those skilled in the art. In some embodiments, the ratio of reaction mixture to hexane to water is 3:1:1 by volume.

The separation may be done by gravity in a separating funnel, wherein three layers are formed with an emulsified phase formed between the upper hexane phase and the lower water phase. The emulsified phase may be mixed with hexane again to further extract fatty acid alkyl esters. The hexane phase containing the fatty acid alkyl esters is further washed by water to remove some impurities such as water-soluble catalysts.

Some other organic solvents immiscible with water may be used instead of hexane, such as petroleum ether, cyclohexane, and the like.

Impurity (Chlorophyll) Removal

The concentration of chlorophyll in crude algal oil is 5,320 to 39,998 ppm, which is 117 to 3,076 times greater than that in canola oil. Due to the large quantity of chlorophyll, the algal oil looks dark green or even black, and the crude algal fatty acid alkyl esters obtained from the transesterification reaction looks dark brown.

The chlorophyll is readily co-extracted by hexane with the fatty acid alkyl esters and may have serious negative impacts on the downstream purification processes. For example, the presence of chlorophyll complicates silica gel column chromatography.

Conventional methods for removing chlorophyll from plant oils include physical absorption, oxidation treatment and phosphoric acid degumming (Issariyakul, T.; Dalai, A. K. Biodiesel Production from Greenseed Canola Oil. Energy Fuels 2010, 24, 4652-4658.; Bahmaei, M.; sadatSabbaghian, E.; Farzadkish, E. Development of a method for chlorophyll removal from canola oil using mineral acids. J. Am. Oil Chem. Soc. 2005, 82, 679-684.; Ghazani, S.; Marangoni, A. Minor components in canola oil and effects of refining on these constituents: A review. J Am. Oil Chem. Soc. 2013, 90, 923-932). Baroi et al. reported that a catalyst improved the quality of the biodiesel by adsorbing chlorophyll from the feedstock (75.56% of chlorophyll removed) during a transesterification reaction (Baroi, C.; Dalai, A. K. Simultaneous esterification, transesterification and chlorophyll removal from green seed canola oil using solid acid catalysts. Catal. Today 2013, 207, 74-85). Another study from Bahmaei et al. showed that concentrations of chlorophyll of up to 30 ppm could be reduced to amounts of less than 0.01 ppm by mixing the crude canola oil with a 0.4 wt % mixture of phosphoric and sulfuric acids (2:0.75, v/v) for 5 min at 50° C. (Bahmaei, M.; sadatSabbaghian, E.; Farzadkish, E. Development of a method for chlorophyll removal from canola oil using mineral acids. J. Am. Oil Chem. Soc. 2005, 82, 679-684). Przybylski et al. reported that the total chlorophyll content of canola oil was reduced to less than 1 ppm after bleaching with activated bleaching clays (Przybylski, R.; Mag, T.; Eskin, N. A. M.; Mc Donald, B. E. Canola Oil. In Bailey's Industrial Oil and Fat Products, 6th ed.; Shahidi, F., Ed.; Wiley-Interscience: Hoboken, N.J., USA, 2005). Typically, the concentration of chlorophyll in crude canola oil is 13-30 ppm (Diosady, L. L. Chlorophyll removal from edible oils. Int. J. Appl. Sci. Eng. 2005, 2, 81-88), which is much lower than the levels found in algae oil.

It has also been found that certain amorphous silicas are particularly well suited for removing trace contaminants, specifically phospholipids and associated metal ions, as well as chlorophyll A, from Jojoba oil, as described in U.S. Pat. No. 5,053,169. The resulting reduction of green coloration is desired for marketing purposes. However, the Jojoba oil is originally light gold in color and contains only a little chlorophyll, which is also much lower than the levels found in algae oil. Acid-treated amorphous silicas are also reported to be particularly well suited for removing phospholipids and/or chlorophyll from glyceride oils to yield oils having commercially acceptable levels of those contaminants, as described in U.S. Pat. No. 5,059,487. The presence of a strong acid in the pores of the silica adsorbent greatly improves its ability to remove chlorophyll. However, the strong acid may finally contaminant the final algal product.

Sometimes, when chlorophyll at a high concentration has to be removed from the algal oil, a chlorophyll adsorbent other than silica has to be employed. Because most of the trace contaminants (soaps and phosphatides, for example) which adversely affect the adsorption of chlorophyll by adsorbents normally used for pigment removal (neutral earths, activated earths and carbons) by fouling, poisoning or competitive adsorption are selectively removed during refining with silica, the effectiveness of the chlorophyll adsorbent can be greatly enhanced when used in conjunction with silica. The combined use of specific adsorbents in this way can lead to improved processing and process control while improving refined oil quality.

As mentioned above, the algal oil contains a high concentration of chlorophyll. Organic solvent extraction and supercritical fluid extraction are used in chlorophyll removal in algal oil. Acetone is not effective in chlorophyll removal while methanol causes formation of chlorophyll a degradation products. Dimethyl formatmide (DMF) is a superior extraction solvent to methanol, ethanol and acetone but is toxic in nature (S. W. Jeffrey, R. F. C. Mantoura, and S. W. Wright, Eds., Phytoplankton Pigments in Oceanography: Guidelines to Modern Methods, UNESCO, Paris, Farnce, 1997.; D. P. Sartory and J. U. Grobbelaar, "Extraction of chlorophyll a from freshwater phytoplankton for spectrophotometric analysis," Hydrobiologia, vol. 114, no. 3, pp. 177-187, 1984.; D. Simon and S. Helliwell, "Extraction and quantification of chlorophyll a from freshwater green algae," Water Research, vol. 32, no. 7, pp. 2220-2223, 1998; R. F. C. Mantoura and C. A. Llewellyn, "The rapid determination of algal chlorophyll and carotenoid pigments and their breakdown products in natural waters by reverse-phase highperformance liquid chromatography," AnalyticaChimicaActa, vol. 151, no. 2, pp. 297-314, 1983).

Supercritical fluid extraction is a more environmentally friendly method for chlorophyll removal than organic solvent extraction, but a set of apparatus is needed, which is power-consuming.

Further, Sathish and Sims (2012) exhibited that a wet lipid extraction procedure was capable of removing most of the chlorophyll contamination in the algal lipid extract through precipitation (Sathish, A.; Sims, R. C. Biodiesel from mixed culture algae via a wet lipid extraction procedure. Bioresour. Technol. 2012, 118, 643-647). Chen et al. showed that treatment with bleaching earth in a rotary evaporator reduced the content of chlorophyll and total carotenoids in Scenedesmus sp. to 40.3 and 199.0 ppm, respectively (Chen, L.; Liu, T.; Zhang, W.; Chen, X.; Wang, J. Biodiesel production from algae oil high in free fatty acids by two-step catalytic conversion. Bioresour. Technol. 2012, 111, 208-214).

It can be seen that the well-known methods mentioned above are not applicable on large scale.

The present inventors have found a method capable of removing almost all of the pigments, including chlorophyll, fucoxanthin and beta-carotene, in one step within several minutes. In particular, in the instant invention, the fatty acid alkyl esters obtained from the transesterification reaction are first extracted using hexane and water, leaving some impurities in the water phase. Then, the hexane phase containing fatty acid alkyl esters is made in contact with silica gel. The hexane makes silica gel affinitive to pigments. With only about five minutes, all or substantially all pigments, with some other impurities, are absorbed by silica gel and then removed from the fatty acid alkyl esters by recovery of silica gels by filtration. Stirring is preferably done to enhance the contact.

A large quantity of silica gels is good for chlorophyll (impurity) removal but will cause loss of PUFAs to some extent. As shown in the Examples below, an optimized amount is there for the silica gel, i.e., the ratio of the crude fatty acid alkyl esters to the silica gel is preferred to be 1:0.75 (ml/g, v/w) or 1:1. With such ratios, 90% or more of PUFAs such as EPA are recovered after impurity removal.

The silica gel used in the invention is of 60 mesh or more, 65 mesh or more, or 70 mesh or more, and 100 mesh or less, 95 mesh or less, or 90 mesh or less. The silica gel can be regenerated simply by ethanol washes.

EXAMPLES

Example 1 Preparation of Algal PUFA Ethyl Esters

Nannochloropsis *salina* grew in artificial sea water in an open pond for 7 days, the artificial sea water containing 22 g/L NaCl, 2.44 g/L $MgSO_4.7H_2O$, 0.6 g/L KCl, 0.25 g/L urea, 0.3 g/L $CaCl_2.2H_2O$, 4.4 mg/L $NaH_2PO_4.2H_2O$, 0.1 g/L $NaHCO_3$, 0.75 mg/L $Na_2EDTA.2H_2O$, 0.097 mg/L $FeCl_3.6H_2O$, 0.5 mg/L $H_3BO_3$, 1 mg/L $MnSO_4$, 0.05 mg/L $ZnSO_4$, 0.02 mg/L $CoCl_2.6H_2O$, and 0.1 mg/L $Na_2MoO_4.2H_2O$.

One ton of algae broth was collected and added with 6M NaOH to change its pH value to 10.5 where algae began to settle down. Three hours later, the upper water layer was discarded, and the remains were subject to filtration using Miracloth having a pore size of 25 μm to obtain 1 kg of algal mud having a water content of 80 wt %. The algal mud was spray dried for 2 hours in a dryer (ZPG-G intelligent Spray Dryer) with air at the inlet having a temperature of 180° C. and air at the outlet being 90° C., and 146 g of dry algae having a water content of 5 wt % or less was obtained.

Figure 1:
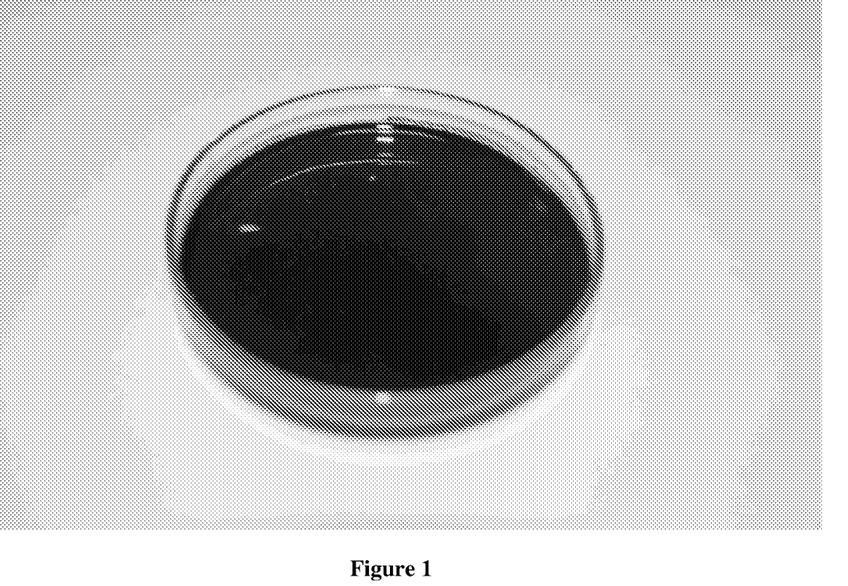
FIG. 1 shows the crude algal oil extracted from dry algae by using ethanol.

Twenty five grams of the obtained dry algae was weighed and then mixed in 250 g of 99.5% ethanol. The resulting suspension was stirred at 78° C. using a magnetic stirrer in a three-neck round-bottom flask connected with a reflux condenser for 30 minutes to extract lipid. Then, filtration was done using a 50 μm pore sized filter paper in a Buchner funnel connected to a suction pump to remove solids, and another 250 g of 99.5% ethanol was added to the solids to repeat the lipid extraction. The lipid-containing liquid was combined with the previously obtained filtrate to provide 641 ml of dark green lipid-containing liquid in total. The dark green liquid was later subject to filtration to remove solids using a 50 μm pore sized filter paper in a Buchner funnel connected to a suction pump, followed by evaporation in a vacuum rotary evaporator at 55° C. under a vacuum degree of −0.07 MPa to remove ethanol. A total of 9.73 g of viscous oil-like crude algal oil was obtained after the evaporation step, as shown in FIG. 1.

The algal oil was then added with 51 ml of 99.5% ethanol and 3.57 ml of 100% sulfuric acid. The mixture underwent a transesterification reaction at 70V for 2 hours. After transesterification, the resulting liquid was added with 20 ml of hexane and 20 ml of water in a separating funnel. Three layers showed up a few minutes later, i.e., an upper hexane phase, a lower water phase and an emulsified phase formed therebetween. The hexane phase containing generated fatty acid ethyl esters was collected and washed by water for 4-5 times until pH became neutral (hexane phase:water=1:1, v/v). The emulsified phase was subject to extraction again using 4 ml of hexane and then washed by water until pH became neutral. Due to inevitable loss of hexane phase in water washes, about 14.7 ml of hexane phase was obtained finally in total, containing about 2.63 g/2.94 ml of crude fatty acid ethyl esters.

Figure 2:
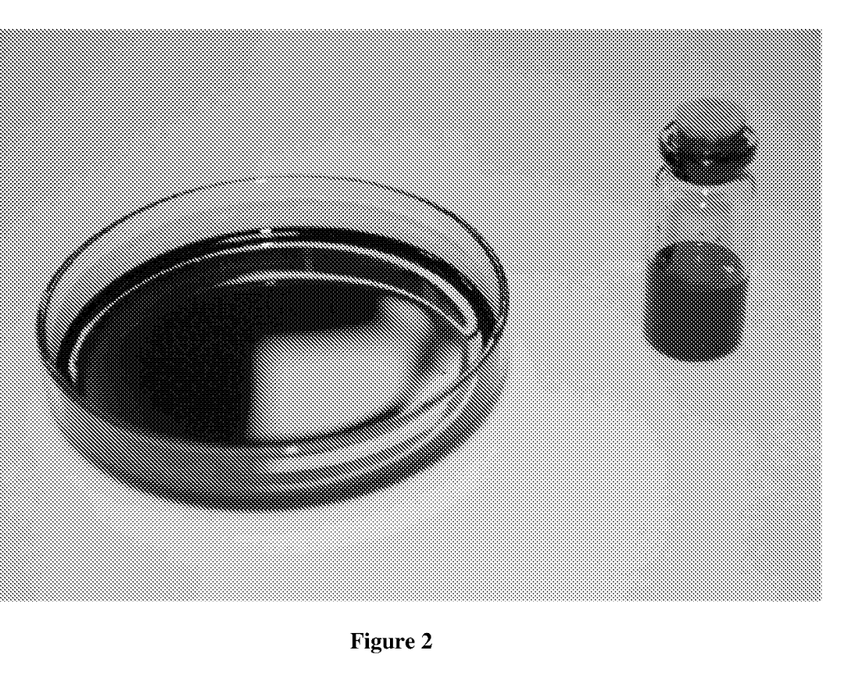
FIG. 2 shows the crude fatty acid ethyl esters with hexane removed, which is extracted using hexane from the transesterification reaction mixture.

When hexane was blown away by continuous flowing nitrogen gas, the crude fatty acid ethyl esters were present as dark brown liquid, as shown in FIG. 2.

Example 2 Purification of Algal PUFA Ethyl Esters

About 14.7 ml of the hexane phase obtained in Example 1 containing about 2.63 g/2.94 ml of crude fatty acid ethyl esters was added with 8.82 g, 5.88 g, 4.41 g, 2.94 or 2.20 g of silica gel (60 to 100 mesh, Column Chromatography Silica Gel (Refined), Qingdao Haiyang Chemical Co., Ltd.) to remove impurities such as chlorophyll. The resulting mixture was fiercely shaken for 5 minutes using a vortex mixer. Thereafter, the hexane phase turned to yellow. The hexane phage was filtered using a 50 μm pore sized filter paper in a funnel at room temperature to remove silica gel. The hexane was then blown away by continuous flowing nitrogen gas to obtain purified fatty acid ethyl esters.

The crude and purified fatty acid ethyl esters were sent to GC analysis. The GC analysis mentioned above was done in a gas chromatograph (Ultra Trace, Thermo Scientific, United States) with a flame ionization detector.

Column: DB-23 (Agilent Technologies, United States)
   60 m×0.25 mm, film thickness 250 nm
Carrier: Nitrogen at 2 ml/min (constant flow)
Oven: 50° C. for 1 min
   50-170° C. at 40° C./min
   170° C. for 1 min
   170-210° C. at 18° C./min
   210° C. for 28 min
Injector: Split 50:1, 270° C.
Detector: FID, 280° C., air at 350 ml/min, $H_2$ at 35 ml/min.

The components in the crude and purified fatty acid ethyl esters were shown in Table 1 below.

TABLE 1

Components in crude/purified fatty acid ethyl esters

| | Crude fatty acid ethyl esters | Purified fatty acid ethyl acids (treated by 2.94 g of silica gel) |
|---|---|---|
| Carotenoids (wt %) | 19% | 25% |
| EE-EPA (wt %) | 22% | 28% |
| EE-other FAs (wt %) | 35% | 47% |
| Impurities (wt %) | 24% | ~0% |

It can be seen from Table 1 that silica gel absorbed almost all of the impurities including chlorophyll, leaving EPA and other fatty acids as well as carotenoids.

Table 2 below showed EPA yield, EPA concentration and also EPA recovery in purified fatty acid ethyl esters treated with different amounts of silica gels.

TABLE 2

EPA yield, concentration and recovery in purified fatty acid ethyl esters

| Silica gel (g) | Hexane phase: Silica gel (ml/g, v/wt) | EPA yield (g) | EPA concentration (wt %) | EPA recovery (%)* |
|---|---|---|---|---|
| 8.82 | 5:3 | 0.31 | 23.21 | 34.35 |
| 5.88 | 5:2 | 0.54 | 26.87 | 59.64 |
| 4.41 | 5:1.5 | 0.82 | 27.52 | 90.33 |
| 2.94 | 5:1 | 0.91 | 28.21 | 100 |
| 2.20 | 5:0.75 | 0.89 | 27.61 | 97.87 |

*EPA recovery = EPA yield in purified fatty acid ethyl esters/EPA yield in crude fatty acid ethyl esters × 100%

Chlorophyll was completely removed from the fatty acid ethyl esters when 8.82 g, 5.88 g or 4.41 g of silica gel was used. However, in these cases, some fatty acid ethyl esters were adsorbed by silica gel and thus lost at the same time, with the EPA recovery being about 90% or even less.

When less, e.g., 2.94 g or 2.20 g of, silica gel was used, a light amount of chlorophyll remained, but more EPA ethyl esters were obtained. The EPA recovery suggested no loss of EPA ethyl esters in impurity removal in these two cases.

Example 3 Production and Purification of Algal PUFA Ethyl Esters on Larger Scale Fatty acid ethyl esters were produced from algae as in Example 1, wherein 700 g of dry algae were used, and the amount of all reagents was scaled up accordingly. Then, the obtained crude fatty acid ethyl esters were purified as in Example 2, with crude fatty acid ethyl esters contacting with 61.6 g of silica gel (Hexane phase:Silica gel (ml/g, v/wt) =5:0.75) for 5 minutes.

Figure 3:
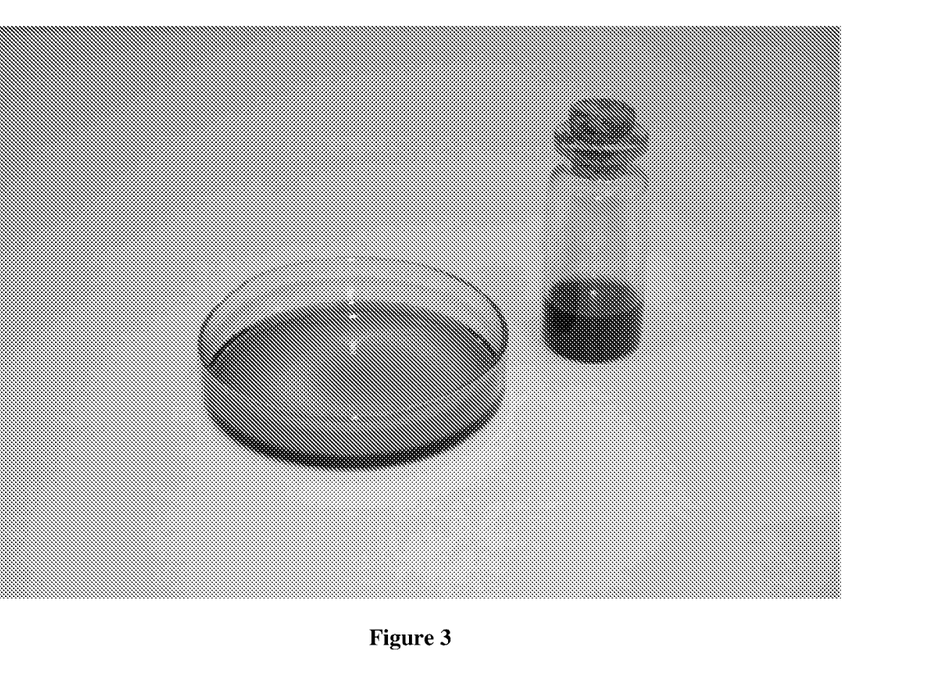
FIG. 3 shows the purified fatty acid ethyl esters, from which hexane is removed.

The purified fatty acid ethyl esters of Example 3, as shown in FIG. 3, contained 25.93 g of EPA ethyl esters whose concentration was 27.46 wt % and recovery was 92.6%, similar to that performed on small scale, suggesting a potential application of the present invention on large scale.

Example 4 De-Flocculation Reduced Salts, Metal Hydroxides and Metal Oxides in Algal Biomass Nannochloropsis *salina* grew in an open pond for 7 days. Then, 1 ton of algae broth was collected and added with about 1042 ml of 6M NaOH to change its pH value to about 10.5 where algae began to settle down. Two hours later, the upper water layer was discarded, and the remains were subject to centrifugation at 5500 rpm for 5 minutes to obtain about 2000 g of sediment having a water content of 85%.

The sediment was added with about 600 ml of diluted HCl (0.5 vol %) to adjust the pH value to about 7.0. The resulting suspension was then added with 2400 ml of water to dissolve sodium chlorides or some other salts, and then sent to centrifugation again at 5500 rpm g for 5 minutes. The upper water layer was discarded and sediment was collected and weighed. About 300 g of sediment having a water content of 85% was obtained, which was spray dried for 2 hours in a dryer with air at the inlet having a temperature of 180° C. and air at the outlet being 90° C. to obtain about 146 g of dry algae having a water content of 5 wt % or less.

As compared to Example 1, the de-flocculation process reduced/removed impurities contained in the algal biomass, including most of sodium chlorides and metal hydroxides/oxides.

Comparative Example 1 Cell Disruption Decreased PUFA Yield/Concentration

Nannochloropsis *salina* grew in an open pond for 7 days. Then, 1 ton of algae broth was collected and added with 6M NaOH to change its pH value to 10.5 where algae began to settle down. Three hours later, the upper water layer was discarded, and the remains were subject to filtration using Miracloth having a pore size of 25 μm to obtain 1 kg of algal mud having a water content of 80%. The algal mud was spray dried for 2 hours in a dryer (ZPG-G intelligent Spray Dryer) with air at the inlet having a temperature of 180° C. and air at the outlet being 90° C., and 146 g of dry algal powder having a water content of 5 wt % or less was obtained.

The obtained dry algae was ground using a grinding machine (CWM20 Vibration milling machine, 380 V/Hz) at 960 rpm to provide a particle size of 2 to 3 μm.

Twenty five grams of the ground algae was weighed. Using the method as described in Example 1, 10.37 g of crude oil was extracted from the algal powder.

The crude oils obtained in Example 1 and Comparative Example 1 underwent a transesterification reaction to convert the natural fatty acids into fatty acid methyl esters. The transesterification reaction was performed as follows. Five mg of the crude oil was transferred to an Agilent flask where 1 ml of 1M sulfuric acid-methanol solution (prepared by adding 5 mL (9.2 g) of concentrated sulfuric acid and 95 mL of 100% methanol) was added. The flask was filled with $N_2$ and heated in boiling water for 1 hour. After cooled down, the flask was introduced with 200 μl of distilled water. Then, 200 μl of n-hexane was used to extract fatty acid methyl esters in a separating funnel. Extraction was performed for 3 times in total, and the collected hexane phases were combined together. Hexane was taken away with flowing nitrogen gas, and the remaining liquid was dissolved in 100 μl of n-hexane. From the resulting solution, 1 μl was picked for GC analysis.

The conditions for GC analysis were the same as those described above.

The crude oil weight and EPA yield/concentration of Example 1 and Comparative Example 1 were listed in Table 3 below.

TABLE 3

Crude oil mass and EPA yield/concentration

| | Oil weight (g) | EPA yield (g) | EPA concentration (wt %) |
|---|---|---|---|
| Example 1 | 9.73 | 0.906 | 9.31 |
| Comparative Example 1 | 10.37 | 0.838 | 8.08 |

Surprisingly, the ground fine algal powder with the cell disrupted led to relatively lower EPA yield or concentration.

The types and concentrations of fatty acids contained in the crude oils of Example 1 and Comparative Example 1 were shown in Table 4 below in detail.

TABLE 4

Types and concentrations of fatty acids in crude oil

|  |  | Example 1 | Comparative Example 1 |
|---|---|---|---|
| Concentration of fatty acids (wt %) | $C_8$ | 0.05 | 0.05 |
|  | $C_{10}$ | 0.03 | 0.02 |
|  | $C_{12}$ | 0.14 | 0.12 |
|  | $C_{13}$ | 0.00 | 0.00 |
|  | $C_{14:1}$ | 0.01 | 0.01 |
|  | $C_{14:0}$ | 1.51 | 1.26 |
|  | $C_{15:1}$ | 0.01 | 0.01 |
|  | $C_{15:0}$ | 0.41 | 0.36 |
|  | $C_{16:1}$ | 5.47 | 4.67 |
|  | $C_{16:0}$ | 6.18 | 5.25 |
|  | $C_{17:1}$ | 0.05 | 0.05 |
|  | $C_{17:0}$ | 0.08 | 0.08 |
|  | $C_{18:3}$ | 0.18 | 0.20 |
|  | $C_{18:n}$ | 1.18 | 1.19 |
|  | $C_{18:0}$ | 0.20 | 0.19 |
|  | $C_{20:5}$(EPA) | 9.31 | 8.08 |
|  | $C_{20:0}$ | 0.05 | 0.05 |
|  | $C_{22:2}/C_{22:1}$ | 0.07 | 0.00 |
|  | $C_{22:0}$ | 0.00 | 0.04 |
|  | $C_{23:0}$ | 0.00 | 0.00 |
|  | $C_{24:0}$ | 0.08 | 0.09 |
|  | Total | 25.02 | 21.71 |

It can be seen from Table 4 that most fatty acids extracted from the ground algal powder had lower concentrations, suggesting a disadvantageous effect of cell disruption.

Comparative Example 2 Less PUFA Ethyl Esters were Obtained if Transesterification was Performed Directly on Algae Nannochloropsis *salina* grew in an open pond for 7 days. Then, 1 ton of algae broth was collected and added with 6M NaOH to change its pH value to 10.5 where algae began to settle down. Three hours later, the upper water layer was discarded, and the remains were subject to filtration using Miracloth having a pore size of 25 μm to obtain 1 kg of algal mud having a water content of 80%. The algal mud was spray dried for 2 hours in a dryer (ZPG-G intelligent Spray Dryer) with air at the inlet having a temperature of 180° C. and air at the outlet being 90° C., and 146 g of dry algal powder having a water content of 5 wt % or less was obtained.

Some of the obtained dry algae were ground using a grinding machine (CWM20 Vibration milling machine, 380 V/Hz) at 960 rpm to provide a particle size of 2 to 3 μm. Twenty five grams of the crude algae and 25 g of ground algae were weighed and then added with 250 g of ethanol (99.5%) and 22.15 ml of sulfuric acid (100%), respectively. The mixtures were left for transesterification reaction at 70° C. for 2 hours with stirring using a magnetic stirrer. Fatty acid ethyl esters were extracted as described in Example 1 using hexane. Hexane was evaporated in vacuum rotary evaporator at 45° C. under vacuum degree of −0.07 MPa, and the remaining crude fatty acid ethyl esters were sent for GC analysis.

The EPA yield and EPA concentration in the crude fatty acid ethyl esters of Example 1 and Comparative Example 2 were shown in Table 5.

TABLE 5

EPA yield and concentration in crude fatty acid ethyl esters

|  | Size of algae | EPA yield (g) | EPA concentration (wt %) |
|---|---|---|---|
| Example 1 | Original algae | 0.9056 | 23.28 |
| Comparative Example 2 | Original algae | 0.3065 | 12.56 |
|  | Ground algae | 0.3442 | 10.24 |

When the transesterification reaction was performed upon extracted algal oil, both EPA yield and EPA concentration were much higher.

Comparative Example 3 Silica Gel was Better in Impurity Removal than Bleaching Clay Fatty acid ethyl esters were produced and purified in the same way as that described in Example 1 and Example 2, except that bleaching clays were used instead of silica gel to remove impurities from the crude fatty acid ethyl esters.

Table 6 below showed the EPA yield, concentration and recovery in the purified fatty acid ethyl esters when different amounts of bleaching clays were used in impurity removal.

TABLE 6

EPA yield, concentration and recovery in purified fatty acid ethyl ester

|  | Bleaching clay (mg) | Hexane phase (ml) | Hexane phase:Bleaching clay (mL/g, v/wt) | EPA yield (g) | EPA concentration (wt %) | EPA recovery (%) |
|---|---|---|---|---|---|---|
| Bleaching clay I | 90 | 0.6 | 5:0.75 | 0.248 | 13.03 | 24.67 |
| Bleaching clay II | 90 | 0.6 | 5:0.75 | 0.2491 | 12.51 | 23.78 |
| Bleaching clay III | 90 | 0.6 | 5:0.75 | 0.2473 | 12.72 | 24.01 |
| Bleaching clay I | 180 | 0.6 | 5:1.5 | 0.2286 | 14.43 | 25.18 |
| Bleaching clay II | 180 | 0.6 | 5:1.5 | 0.2453 | 17.85 | 33.43 |
| Bleaching clay III | 180 | 0.6 | 5:1.5 | 0.2275 | 15.88 | 27.58 |

Bleaching clay I (Enhanced version; Jun Chen bentonite technology co. LTD; 200 mesh); bleaching clay II, (Standard edition; Jun Chen bentonite technology co. LTD; 200 mesh); bleaching clay III, (Special version; Jun Chen bentonite technology co. LTD; 200 mesh)

The bleaching clays' impurity (e.g., chlorophyll) removal capacity was inferior to that of silica gels. Further, EPA yield and concentration were much lower when the bleaching clays were used, as shown in Table 6. The EPA recovery also indicated that a lot of PUFAs were lost in impurity removal using bleaching clays.

The invention claimed is:

1. A method for producing purified algal oils containing eicosapentaenoic acid (EPA) comprising:

a) contacting with ethanol dry algae of the genus Nannochloropsis, wherein the Nannochloropsis dry algae has intact cell walls and a water content of 5 wt % or less, to obtain an ethanol solution;
b) removing solids from the ethanol solution to obtain a crude oil;
c) subjecting the crude oil to a transesterification reaction with a lower alcohol to generate fatty acid alkyl esters;
d) extracting with hexane the fatty acid alkyl esters to result in a hexane phase containing fatty acid alkyl esters; and
e) purifying the hexane phase containing fatty acid esters to remove impurities including chlorophyll to obtain the purified algal oils containing the EPA by contacting the hexane phase containing fatty acid esters with silica gel in a hexane to silica gel ratio (ml/g, v/wt) of about 5:1.5 or more, whereby EPA recovery is greater than 90% and the purified algal oils containing EPA has ~0% impurities including ~0% chlorophyll.

2. The method of claim 1, wherein the dry algae is obtained by flocculating algal cells out of its liquid cultural medium by adjusting the pH of the medium to about pH 10.5, collecting algal mass via centrifugation or filtration, and then drying the algal mass.

3. The method of claim 1, wherein the dry algae is obtained by flocculating algal cells out of its liquid cultural medium by adjusting the pH of the medium to about pH 10.5, collecting algal mass via centrifugation or filtration, re-adjusting the pH of the algal mass to about pH 7, and desalting and drying the algal mass.

4. The method of claim 1, wherein the algae is Nannochloropsis sauna.

5. The method of claim 1, wherein the contacting in step a) comprises mixing the dry algae in 99.5% ethanol at a ratio of 1:10-1:5 by weight for 30 minutes at 78° C.

6. The method of claim 1, wherein ethanol is removed in step b) by filtration and/or evaporation.

7. The method of claim 1, wherein, the transesterification reaction is performed in the presence of sulfuric acid at 70° C. for 2 hours, and the lower alcohol is selected from the group consisting of methanol, ethanol, propanol and butanol.

8. The method of claim 1, wherein, the fatty acid alkyl esters are extracted in step d) using a hexane to water ratio of 3:1:1 by volume.

9. The method of claim 1, wherein, the ratio of the phase containing fatty acid alkyl esters to the silica gel is about 5:1.5 (ml/g, v/w).

10. The method of claim 1, wherein, the method further includes
f), recovering the silica gel.

11. The method of claim 1, wherein, the fatty acid alkyl esters comprise EPA alkyl ester, and ARA alkyl ester.

* * * * *